United States Patent
Jean et al.

(10) Patent No.: US 11,519,870 B2
(45) Date of Patent: Dec. 6, 2022

(54) METHOD AND SYSTEM FOR DETERMINING AN EXPOSURE TEMPERATURE OF AN ENGINE COMPONENT USING LUBRICATION FLUID ANALYSIS

(71) Applicant: PRATT & WHITNEY CANADA CORP., Longueuil (CA)

(72) Inventors: Maurice Jean, Morin-Height (CA); Nathalie Savard, St-Jean-sur-Richelieu (CA); Sonia Sevigny, Brossard (CA); Stéphanie Pronovost, Chambly (CA)

(73) Assignee: PRATT & WHITNEY CANADA CORP., Longueuil (CA)

(*) Notice: Subject to any disclaimer, the term of this patent is extended or adjusted under 35 U.S.C. 154(b) by 623 days.

(21) Appl. No.: 16/562,520

(22) Filed: Sep. 6, 2019

(65) Prior Publication Data
US 2021/0063327 A1    Mar. 4, 2021

Related U.S. Application Data

(60) Provisional application No. 62/892,814, filed on Aug. 28, 2019.

(51) Int. Cl.
  *G01N 33/28* (2006.01)
  *G01N 23/223* (2006.01)
  *F01D 25/00* (2006.01)
  *G07C 5/08* (2006.01)

(52) U.S. Cl.
  CPC ......... *G01N 23/223* (2013.01); *F01D 25/002* (2013.01); *G01N 33/2858* (2013.01); *G01N 33/2888* (2013.01); *G07C 5/0808* (2013.01); *G01N 2223/635* (2013.01)

(58) Field of Classification Search
  CPC ............ G01N 23/223; G01N 33/2858; G01N 33/2888; G01N 2223/635; G07C 5/0808; F01D 25/002
  See application file for complete search history.

(56) References Cited

U.S. PATENT DOCUMENTS

| 5,889,200 A | 3/1999 | Centers et al. |
| 9,897,582 B2 | 2/2018 | Jean et al. |
| 2003/0213292 A1* | 11/2003 | Budeiri ............. G01N 33/2888 73/114.57 |

(Continued)

FOREIGN PATENT DOCUMENTS

EP    3521794 A1    8/2019

OTHER PUBLICATIONS

European Patent Office, Communication re. extended European search report for European patent application No. 20193213.4, dated Apr. 6, 2021.

*Primary Examiner* — Eric S. McCall
(74) *Attorney, Agent, or Firm* — Norton Rose Fulbright Canada LLP

(57) ABSTRACT

Systems and methods are provided for determining an exposure temperature in an engine. One or more particles filtered from lubrication fluid of an engine may be analyzed. The chemical composition of filtered particles may be compared to reference data which includes a relationship between chemical composition and exposure temperature. An estimate of the exposure temperature may be determined. An output may be generated based on the exposure temperature.

20 Claims, 6 Drawing Sheets

(56) References Cited

U.S. PATENT DOCUMENTS

| | | | |
|---|---|---|---|
| 2013/0080085 A1 | 3/2013 | Von Herzen et al. | |
| 2014/0121994 A1 | 5/2014 | Jean et al. | |
| 2015/0346181 A1* | 12/2015 | Isenberg | G01N 33/2888 |
| | | | 73/114.55 |
| 2016/0003794 A1* | 1/2016 | Basu | G01N 33/2888 |
| | | | 702/30 |
| 2016/0370341 A1 | 12/2016 | Jean et al. | |
| 2017/0159485 A1* | 6/2017 | Jean | G01M 15/14 |
| 2018/0023414 A1* | 1/2018 | Hagen | G01N 33/2858 |
| | | | 73/53.05 |
| 2018/0073970 A1* | 3/2018 | Hagen | F01D 21/10 |
| 2018/0107203 A1* | 4/2018 | Hagen | G01N 33/2858 |
| 2019/0162687 A1* | 5/2019 | Best | F02C 7/06 |
| 2019/0277756 A1* | 9/2019 | Foord | G01N 21/15 |
| 2020/0392863 A1* | 12/2020 | Jean | G01N 15/0618 |
| 2020/0393082 A1* | 12/2020 | Jean | F01D 25/18 |

\* cited by examiner

134

| Temperature (°C) | Element | Estimated composition |
|---|---|---|
| Room temp. | Cu | 93 |
| | Zn | 2 |
| | Sn | 5 |
| 100 | Cu | 93 |
| | Zn | 2 |
| | Sn | 5 |
| 200 | Cu | 93 |
| | Zn | 2 |
| | Sn | 5 |
| 300 | Cu | 92 |
| | Zn | 3 |
| | Sn | 5 |
| 400 | Cu | 90 |
| | Zn | 4 |
| | Sn | 6 |
| 500 | Cu | 85 |
| | Zn | 8 |
| | Sn | 7 |
| 600 | Cu | 76 |
| | Zn | 17 |
| | Sn | 7 |
| 700 | Cu | 65 |
| | Zn | 30 |
| | Sn | 5 |

FIG. 5

METHOD AND SYSTEM FOR DETERMINING AN EXPOSURE TEMPERATURE OF AN ENGINE COMPONENT USING LUBRICATION FLUID ANALYSIS

FIELD

This relates generally to engine diagnostics and more particularly to systems and methods for diagnosing engine conditions using oil (or other lubricant) analysis.

BACKGROUND

Monitoring the temperature of engine oil is known. An oil temperature above an expected range may indicate that an engine is not operating properly. However, monitoring the temperature of engine oil may only provide an average temperature of the oil but may not identify the specific source of additional heat within the engine.

SUMMARY

According to an aspect, there is provided a computer-implemented method for determining an exposure temperature in an engine, the method comprising: receiving input data representative of a chemical composition of a particle filtered from a lubrication fluid of the engine; using one or more data processors: comparing the chemical composition of the particle with reference data including a relationship between the chemical composition and the exposure temperature of the particle; based on the comparing, determining the exposure temperature of the particle; and generating an output based on the exposure temperature of the particle. A maintenance action relative to the engine may be performed based on the output.

According to another aspect, there is provided a system for determining an exposure temperature of a component of an engine, the system comprising: one or more processors; one or more computer-readable storage media having stored thereon processor-executable instructions that, when executed by the one or more processors, cause the one or more processors to perform operations comprising: receiving input data representative of a chemical composition of a particle filtered from a lubrication fluid of the engine; using the chemical composition of the particle, identifying the component of the engine associated with the particle; comparing the composition of the particle with reference data including a relationship between the chemical composition and the exposure temperature of the component; based on the comparing, determining the exposure temperature of the component; and generating an output based on the exposure temperature of the component.

According to another aspect, there is provided a method for improving a condition of an engine, the method comprising: receiving input data representative of a composition of a particle filtered from a lubrication fluid of the engine; determining an exposure temperature of a component of the engine based on the composition of the particle; generating an output representative of a diagnosis of the condition of the engine based on the exposure temperature of the component; and performing a maintenance action on the engine to improve the condition of the engine.

Other features will become apparent from the drawings in conjunction with the following description.

BRIEF DESCRIPTION OF DRAWINGS

In the figures which illustrate example embodiments,

FIG. 5 is a table depicting example reference data; and

DETAILED DESCRIPTION

Figure 1:
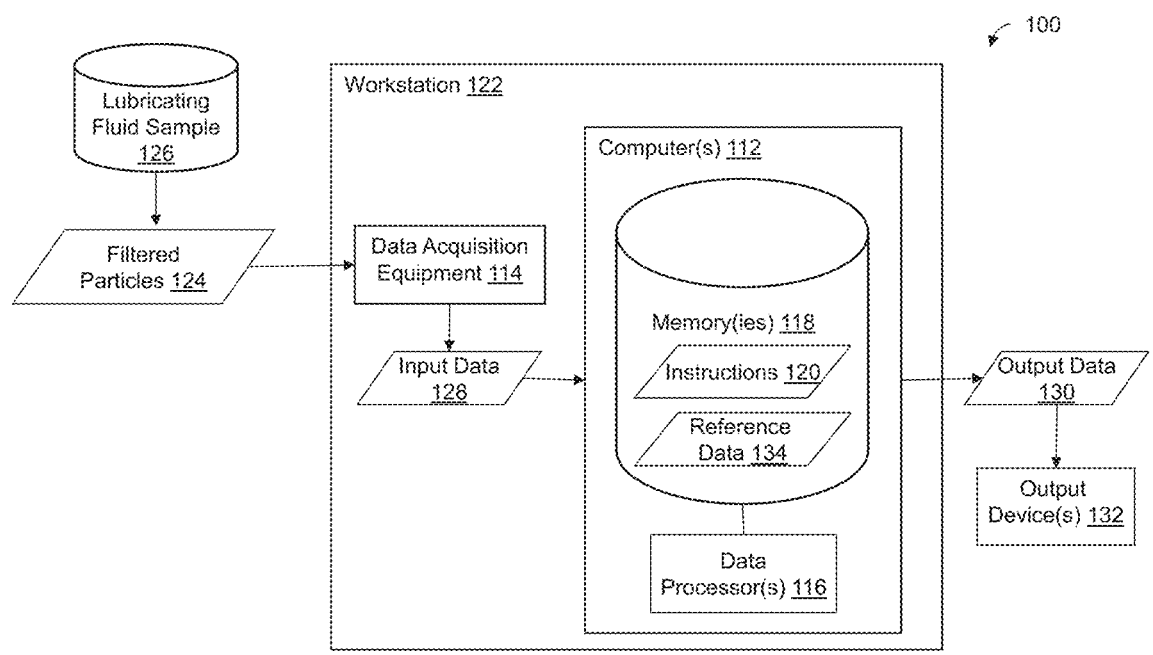
FIG. 1 is schematic diagram of an exemplary system for determining an exposure temperature of a fluid in an engine such as a gas turbine engine.

The present disclosure relates to engine diagnostics using lubricating fluid analysis. In various aspects disclosed herein, such lubricating fluid analysis may use chemical composition of particles as well as the mass of particles and proportion by mass of particles for use in determining an exposure temperature or temperature reached by the fluid, engine, or a component of the engine, and/or diagnosing a condition of an engine.

Recently developed engines, such as gas turbine engines for aircraft applications, may produce debris (e.g. metallic debris) in oil samples at levels of concentration and particle sizes below the operating zone of conventional oil analysis techniques. However, the analysis of such debris may still be useful in diagnosing or determining conditions of such engines.

Oil analysis has been performed for predictive maintenance (e.g., on engines) for quite some time but has limited capability in detecting abnormal behavior early in the process. For example, using conventional techniques, failure is typically detected only hours before a problem occurs, resulting in the need for an engine operator to submit oil samples at short time intervals (e.g. every 10 to 50 hours) to have a chance at capturing the indication of failure before the actual failure occurs. Such a high frequency of sampling may not be practical or economical for an aircraft operator. Moreover, certain operating conditions (e.g. higher than expected temperatures caused by friction or insufficient lubrication to one or more components) may accelerate the process of component failure.

Considering the direct and indirect costs of any engine failure and unplanned engine removal, there is a need for methods and systems that may be able to identify problematic engine operation sufficiently in advance, in order for the appropriate tasks (e.g., corrective action), such as maintenance and/or decommissioning, to be scheduled and carried out.

One conventional approach for monitoring engine material wear is to perform an analysis on particles extracted from the engine filter, where the extracted particles are then analyzed by spectroscopy techniques. This is relatively costly because the engine filter is typically not reused. Further, such a method may not be practical considering that removing the engine filter may be time consuming. For such reasons, among others, filter analysis typically is not performed frequently and is mainly used to monitor engines already identified as potentially behaving abnormally. Filter analysis typically is not suitable for routine monitoring of engines.

Another method is to analyze particles collected from the oil by a magnetic drain plug where the magnetic particles collected by the drain plug are removed and analyzed.

Another conventional approach to monitoring engine wear is to monitor the oil temperature of an engine. However, since oil is circulating through different areas of an engine, this offers at best an average temperature of the oil, and does not provide an indication of whether greater temperatures than the average temperature were experienced in different areas, or by the engine, nor of an exposure temperature of the particles contained in the oil.

The disclosure describes methods and systems for engine diagnostics (e.g. determining an exposure temperature or a temperature reached by an engine, a component of an engine, or by lubricant in an engine) using oil or other lubricating fluids. In various aspects, for example, the disclosure describes methods and systems for determining engine and lubricant temperatures and operating conditions using analysis of particles obtained (e.g. filtered) from oil samples, such as from gas turbine engines.

In various examples and aspects, the disclosed methods and systems may allow for analysis of engine oil (or other lubricant) samples in order to detect abnormal behavior (e.g. exposure temperatures outside of expected ranges during operation) without having to remove the engine filter.

The filtering of particles from an oil sample obtained from the engine may provide an indication of the temperature reached by the oil, engine, and/or a component of the engine during operation of the engine. The presence of certain particles having certain chemical compositions in certain proportions may allow for the determination of an exposure temperature reached by the engine component from which the particle originated, regardless of whether the engine has been turned off and has cooled down to a lower temperature.

Oil samples may be collected at intervals to monitor the status of the engine or oil temperature during operation. In comparison with the oil filter method, the use of an oil sample may permit smaller particles to be considered in the diagnosis as opposed to being limited to a range of particle sizes captures by the filter. In comparison to the magnetic drain plug method, the use of a fluid sample may permit for both magnetic and non-magnetic (e.g. Tin, Copper, Lead) particles to be considered in the analysis.

Accordingly, the disclosed methods and systems may be based on the analysis of relatively small particles in oil that typically are not captured by a conventional 30 micron porosity fluid filter of the engine. By extending the oil analysis to include smaller particles, the disclosed methods and systems may provide better understanding of engine behavior using a relatively small oil sample.

In various embodiments, the methods and systems described herein may make use of methods, steps and/or components of systems described in U.S. Patent Publication Nos. 2014/0121994 (now granted as U.S. Pat. No. 9,897, 582) and 2016/0370341, the contents of which are incorporated by reference in their entireties.

FIG. 1 is a schematic diagram of an exemplary system 100 for determining a temperature experienced by an engine such as a gas turbine engine which uses a fluid for lubricating some of its components, such as bushings, sleeve bearings, gears, and the like. System 100 may comprise one or more computer(s) (referred to herein as "computer 112") and suitable data acquisition equipment 114 of known or other type. Computer 112 may comprise one or more data processors 116 which may be any programmable data processing apparatus of known or other type, or other devices to cause a series of operations to be performed by computer 112 or other device(s) to perform one or more computer-implemented methods.

Computer 112 may also comprise one or more memories (referred to herein as "memory 118"), which may include a suitable combination of any type of computer memory that is located either internally or externally such as, for example, random-access memory (RAM), read-only memory (ROM), compact disc read-only memory (CD-ROM), electro-optical memory, magneto-optical memory, erasable programmable read-only memory (EPROM), electrically-erasable programmable read-only memory (EEPROM), ferroelectric RAM (FRAM), or the like. Memory 118 may comprise any storage means (e.g. devices) suitable for retrievably storing machine-readable instructions 120 executable by data processor 116. Memory 118 may comprise tangible, non-transitory media.

Computer 112 and data acquisition equipment 114 may be considered part of a workstation 122. Accordingly, data acquisition equipment 114 may comprise a scanning electron microscope (SEM), an atomic emission spectrometer (AES), an optical atomic spectrometer (OAS), and/or an atomic absorption spectrometer (AAS), although any other suitable devices/methods for extracting the relevant information from particles 124 filtered from lubricating fluid sample 126 may be used. In some embodiments, data acquisition equipment 114 may comprise an SEM and an X-Ray Fluorescence (XRF) detector for carrying out particle analysis. For example, data acquisition equipment 114 may comprise an automated SEM, such as that from Aspex Corporation. In some embodiments, the automated SEM may not requirement presence of a human to select the particle(s) that will be analyzed. In some embodiments, software and/or hardware included in workstation 112 may automatically recognize the presence of a particle 124 and may then automatically move a stage and/or an electron beam to the particle(s) 124 on which to perform the analysis.

System 100 may be used to conduct analysis of particles 124 filtered from lubricating fluid sample 126. Data acquisition equipment 114 may be used to analyzed filtered particles 124 and generate input data 128. Input data 128 may be processed using computer 112 according to instructions 120 in order to generate output data 130. In some embodiments, output data may be representative of a temperature reached by the engine, an exposure temperature of a component of the engine, and/or a temperature of a fluid sample and may be delivered to a user of system 100 or other authorized party via output device(s) 132 (e.g., one or more screens and/or printers, or other output devices) for displaying and/or otherwise providing a report or indication of the result(s) of the analysis.

System 100 may include one or more input devices (e.g., keyboard, mouse, touchscreen) for receiving user input, as well as one or more data ports and/or communication ports for receiving and/or transmitting data (e.g., wirelessly or through wired connections) from/to other processors, systems and/or devices. Processing of input data 128 by computer 112 may make use of reference data 134 for comparison purposes. It is understood that processing of input data 128 may be performed using one or more processors external to workstation 122.

In some embodiments, example particles 124 may be particles from the surface of a component (e.g. bushings, bearings, contact points between bushings and gears, or the like) of the engine made of an alloy. For example, if an area of the engine is poorly lubricated or experiencing friction or general wear, particles from a surface of a component made of an alloy may be rubbed off, resulting in the presence of debris particles in the lubricating fluid.

Figure 2:
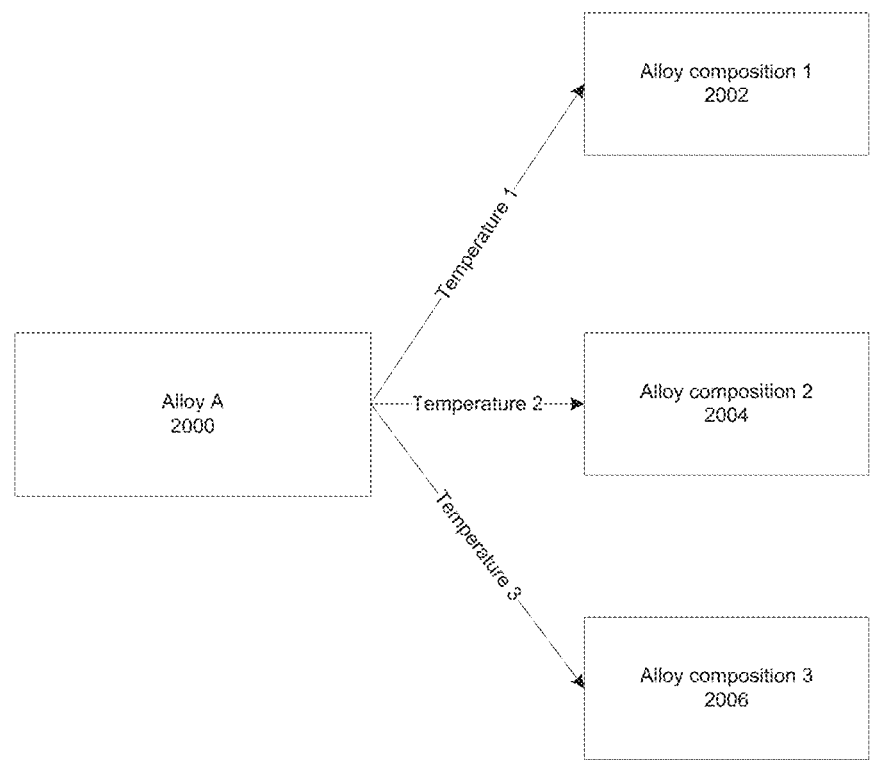
FIG. 2 illustrates a simplified relation between an alloy composition as a function of temperature.

The composition of certain alloys may be a function of temperature, particularly at an outer surface of such alloys. That is, the composition at a surface of a component made of an alloy may vary with temperature. FIG. 2 is a simplified example showing a relationship between the composition of an alloy and temperature. As shown, an example alloy A 2000 may have a first composition 2002 at a first temperature, a second composition 2004 at a second temperature, and a third composition 2006 at a third temperature. Some embodiments may define an exposure temperature experienced by the engine based on alloy composition, as some alloy compositions will change with temperature increases. In some embodiments, it might not be possible to confirm a specific maximum temperature reached by the engine. However, it may be possible to determine that that the exposure temperature reached at least a minimum temperature, or a range of temperatures. In some embodiments, it may be possible to estimate a maximum exposure temperature reached, or a range of temperatures reached.

As an example, if the alloy is leaded bronze (an alloy of tin (Sn), copper (Cu) and lead (Pb), at 1000 degrees Celsius the composition at an outer surface of the component may be around 75% lead, 20% copper and 5% tin. At 300 degrees Celsius, there may be only 5-10% lead at the surface. In some embodiments, a relationship between chemical composition of a particle and an exposure temperature of the component from which the particle was released may be expressed as a function of the amount of lead contained in the particle. In some embodiments, the increase in proportion of lead in collected particles may start around 350 degrees Celsius, as the lead may start separating from the alloy and migrate toward the outer surface of the component.

Figure 3:
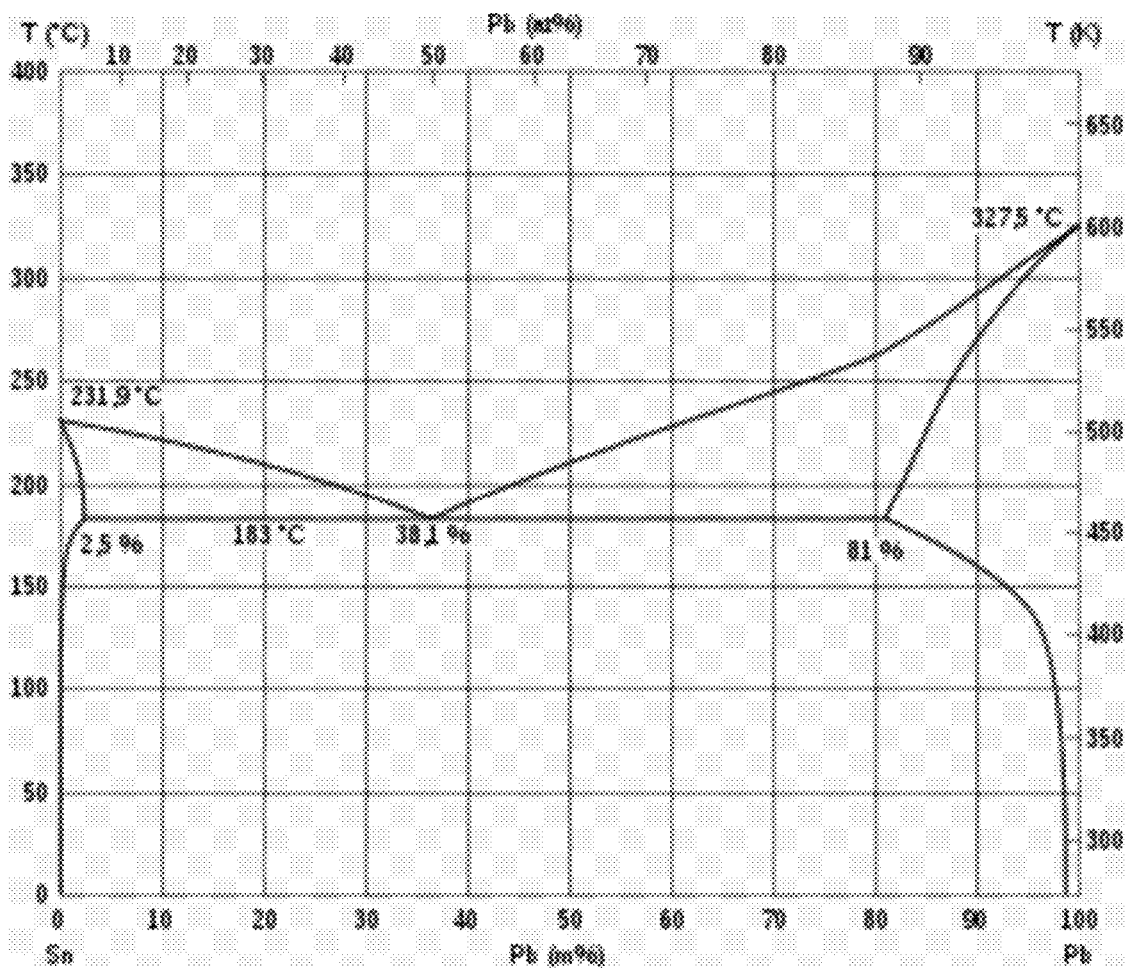
FIG. 3 illustrates an example phase diagram for an example alloy.

FIG. 3 is a phase diagram for leaded bronze illustrating how changes in composition by mass of leaded bronze affect the melting point. Each line in the phase diagram is an isotherm which delineates alloy compositions at different temperatures and can be used to establish a relation between the chemical composition of an allow particle and the temperature at which the particle was generated. Such phase diagrams are available for many alloys, including, for example, alloys including combinations of copper, zinc and lead. FIG. 3 shows 2 elements (lead and tin) as a function of temperature. For example, as depicted in FIG. 3, for an alloy with a composition of 30% tin, the tin may start to separate from the alloy around 183° C., resulting in particles with increasing levels of tin as temperature increases. Similar principles may be applied to more complex alloy systems.

Although some examples described herein relate to leaded bronze, it will be appreciated that principles and embodiments described herein can be applied to any material for which a relationship between chemical composition and temperature is known.

As noted above, engines such as gas turbine engines may produce debris in oil samples. Such debris may include particles from the surfaces of components made of alloys due to friction and/or wear, particularly wear at high temperatures. Given that the surface composition of an alloy may vary with temperature, embodiments described herein may allow for a determination of an exposure temperature reached by the oil, the engine, and/or a component of the engine based on analysis of particles filtered from the oil or other lubricant.

Figure 4:
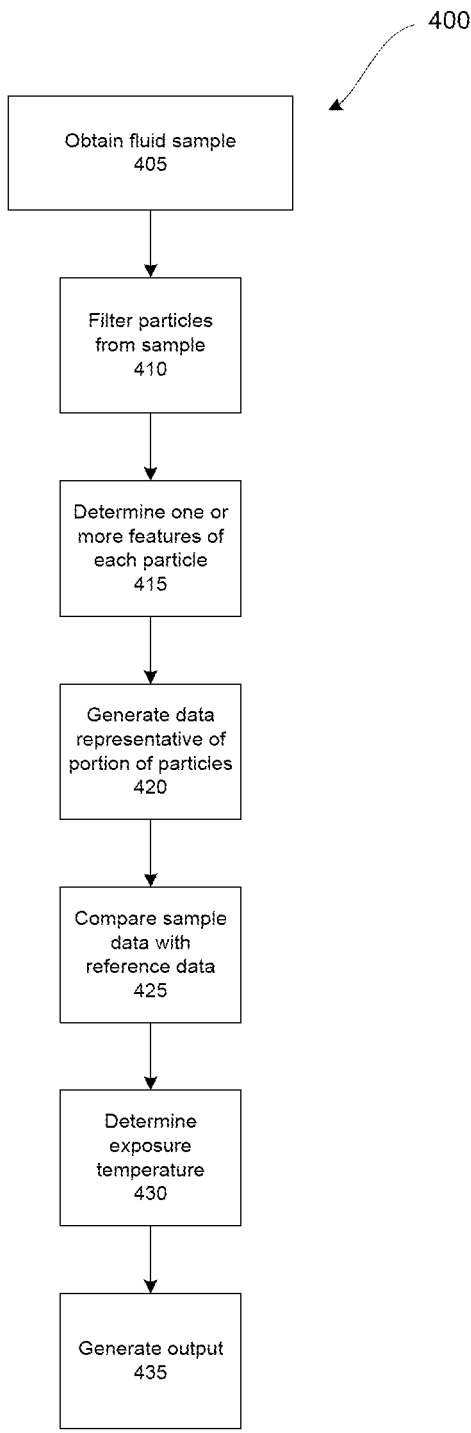
FIG. 4 is a flowchart illustrating an example method for estimating an exposure temperature in an engine.

FIG. 4 is a flowchart illustrating an exemplary method 400 for determining a temperature reached by a fluid sample in an engine using analysis of fluid sample 126, such as engine oil or other lubricant of the engine. Method 400 may be carried out entirely or in part using system 100 based on instructions 120. In some embodiments, depending on the configuration of system 100, some or all of method 400 may be automated (e.g., computer-implemented).

At 405, fluid sample 126 (e.g. an oil or other lubricant sample from an aircraft engine) is obtained. In the example of an oil sample from an aircraft engine, fluid sample 126 may be collected by maintenance personnel of the associated aircraft operator. Accordingly, fluid sample 126 may comprise a relatively small volume of fluid extracted from a relatively larger source of fluid of the engine. In some embodiments, more than one sample 126 may be collected from the engine. In some embodiments, a relatively small amount of oil (e.g., 25 mL or less) may be sufficient. The quantity of oil obtained may be selected in order to obtain a desired number of particles 124 for analysis. For example, it may be known or expected that a particular type of engine should have a certain density of particles in the oil after a certain number of operating hours. Accordingly, the volume of the fluid sample 126 obtained may thus be determined in order to obtain at least 1000 particles, for example. The frequency of sampling may be determined based on the flight/operating hours per year, the maturity of the engine, the typical behavior of the engine type and/or history of unscheduled engine removal for that engine type, for example. The sample 126 may be obtained and prepared using any suitable known or other method.

At 410, sample 126 is filtered using any suitable known or other method to obtain particles 124 from the fluid sample 126. For example, a collected fluid sample 126 may be filtered using a very fine filter, such as a 0.22 micron filter, in order to filter out even very small particles 124 (e.g. particles sized as small as 0.2 microns in diameter or smaller). Using such a filter, a fluid sample 126 of about 25 mL may be sufficient to produce a surface sample of particles 124 of about 16 mm in diameter and suitable for data acquisition via workstation 122 for example. The particles 124 obtained may range in size from about 0.2 microns to 1600 microns, for example, although smaller or larger particles 124 may also be obtained and used in method 400.

The volume of fluid sample 126 used and the size of the sample of particles 124 prepared may vary according to the number of particles 124 in the fluid sample 126. The volume of fluid sample 126 that is used may be determined based on the type of engine and/or the expected normal levels of particles in the oil. In some embodiments, the density of particles 124 of the surface sample of particles may be about 500 particles 124 per square mm, which may be the maximum density that can be used, to reduce or avoid the likelihood of overlapping particles 124. It may be useful to reduce or avoid overlapping particles since two or more particles that overlap with each other may be incorrectly identified as one larger particle, which may lead to incorrect identification and elemental analysis. For example, depending on the density of the sample of particles 124, about 5-10% of particles 124 analyzed may not be identifiable typically due to overlapping and such particles 124 may consequently be excluded from the analysis. In some embodiments, this exclusion rate may be acceptable.

At 415, some or all particles 124 filtered from fluid sample 126 are analyzed using data acquisition equipment 114 to acquire input data 128 from particles 124. Input data 128 may comprise one or more geometric parameters (e.g., shape, size, volume, one or more dimensions) and/or chemical composition information (e.g., element identification, alloy identification, material type) for each particle 124 analyzed. The one or more geometric parameters and the chemical composition may be acquired substantially automatically or semi-automatically depending on the configuration of workstation 122. For example, in some embodiments, data acquisition equipment 114 may be at least partially controlled by computer 112. Any other suitable equipment may be used to generate input data 128.

In some embodiments, a subset of the particles 124 (e.g., 10% or less) may be analyzed and may be sufficient to provide a good representation of the sample of particles 124 as a whole. For example, input data 128 acquired for the subset may be normalized to reflect/estimate the results for the whole sample of particles 124. The analysis of a subset of particles 124 may reduce processing time.

For an average fluid sample 126, about 1500 to 2000 particles 124 may be analyzed. Suitable image analyzer software, such as that conventionally used with a SEM, may be used to collect data about particle characteristics and/or composition. Analysis of each particle 124 may produce a respective set of data for each particle 124. For example, in some embodiments, there may be up to 70 data points associated with each particle 124 for representing the various features of the particle 124 (e.g., size, shape, composition, and the like). The total number of data points obtained from analysis of a single sample may be significantly greater than in conventional oil analysis techniques.

Input data 128 obtained from this analysis may be further processed in order to account for any measurement error and/or the possible presence of contamination. This further processing may include categorizing the particles 124 as described below.

At 420, each particle 124 may be categorized based on the determined features (e.g., geometric parameter and/or chemical composition). The particles 124 may be categorized in different categories, which may be defined according to one or more of: chemical composition categories (e.g., elemental and/or alloy composition), geometric parameters (e.g., size, morphology) and mass. In some embodiments, the identifying of a particular engine component from which the particle originated is contemplated. For example, a particle with a chemical composition which matches a material found in a particular engine component may be identified as having originated from that particular engine component. As another example, morphology of a particle 124 may be determined by calculating an aspect ratio for the particle 124 (e.g. a length to width ratio, where a ratio close to 1 may indicate the particle 124 is close to having a spherical shape while a larger value, such as 10, may indicate that the particle 124 is close to a long fiber shape). As another example, particles may be classified in categories such as "environmental", "metallic", "non-metallic", "plating", or "miscellaneous", among others. Each particle 124 may be further categorized into sub-category levels.

As an example, the "metallic" category may have a level 1 sub-category of "copper", within which may be level 2 sub-categories of "bronze" and "brass". In some embodiments, five levels of decisions may be used to categorize each particle 124 into a specific level (e.g., metallic, copper, bronze, leaded bronze, or machining chip).

Categorization of particles may be based on, for example, the absolute chemical composition, the ratio of some elements, the correlation between a specific standard and particle 124, the size of particle 124, the shape of particle 124 and/or the mass of particle 124 or of some element(s) contained in particle 124. Categories may be defined according to different alloy compositions, association with one specific manufacturing process and/or association with one particular source (e.g. engine component), for example. Categories may also be defined by the elemental composition or single material of the particles 124.

In some embodiments, particles 124 may be categorized as a particular type of alloy (e.g. leaded bronze). Within the leaded bronze category, different particles may have different alloy compositions. Different alloy compositions for the same alloy may be a result of different operating temperatures which cause a change in composition at the surface of certain alloys. For example, a first area of the engine may be hotter than a second area of the engine. As such, the composition at the surface of a component made of leaded bronze alloy may be different in the first area compared to the second, cooler area. Moreover, the temperature within the engine may change over time. For example, the ambient temperature within a given area of an engine may be cooler when the engine has just been started, and the ambient temperature may continue to rise as the engine has been running for a period of time.

Categorization of each particle 124 may be carried out using an algorithm to match each particle to the appropriate category. Each particle may be compared against a historical standard for a category, in order to determine if that particle 124 belongs in that category. Example algorithms for carrying out this categorization include the use of a cross probability match (CPM) index, as well as logical exclusion tests, as described, for example, in U.S. Patent Publication No. 2016/0370341, the contents of which are incorporated by reference in their entirety.

In some embodiments, a category (also referred to as a group of interest) may further break down into one or more bins defined according to particle size ranges. For example, particles 124 may be categorized in columns according to size (in microns, in the example shown) and in rows according to composition. In some embodiments, particles 124 may also be sorted into bins according to particle morphology. The categories may be defined based on elemental composition, alloy type, particle origin, or any other suitable category of particle characteristics and composition. Categorizing particles 124 by size, shape and/or mass, as well as composition may allow for distinguishing between one failure mechanism that is characterized by small particles 124 of the same given alloy, for example. Categorizing particles 124 into categories other than simple elemental composition may also allow for discerning particle data patterns that may not be otherwise observed.

For example, a category may represent a generic type of alloy, and may include one or more levels of sub-categories that may further split the category into finger categorization, for example as precisely as the alloy unified number (UNS) of the particles analyzed. For example, a specific alloy may cover two or more categories and/or sub-categories.

Example categories and sub-categories include but are not limited to:

Environmental—sub-categories: calcium, sodium, CalSil (which may originate from cement from an airstrip), dust— earth, talc, vermiculite (which may originate from packaging of the sample) and chlorides (with further sub-category NaCl).

Metallic—sub-categories: iron (which may include further sub-categories of different composition zones such as different steels, and other alloy types), nickel, titanium, copper (with further sub-categories such as brass, bronze, and leaded copper), zinc (which may originate from galvanized coating found in the engine filters and is typically found with iron and phosphorus particles also), aluminum, magnesium, cobalt and chromium.

Non-metallic: sub-categories: aluminum/silicon, silicon/aluminum, silicon/magnesium, magnesium/aluminum, fiberglass, asbestos, filter fibers, glass beads, and silica.

These exemplary categories may be predefined based on knowledge or expectation of what kind of particles 124 would be obtained from a fluid sample 126 of a given engine type. The categories may also be defined based on the analysis of the samples. For example, if it appears that most of the particles 124 fall into a few categories, sub-categories may be defined for those few categories in order to more finely categorize the particles 124. The defined categories may be different for different engine types and/or at different total operating hours, for example.

At 425, the data obtained from categorization of particles 124 is compared with reference data 134, which may include historical data associated with the engine type (e.g. other engines, fleet data), any data from previous analyses of the same engine, and/or mappings between compositions of an alloy and temperature. FIG. 5 is a table depicting example reference data which may be used to generate an estimation of exposure temperature based on composition. As depicted, FIG. 5 contains a mapping between temperature to the compositions of Copper (Cu), Zinc (Zn) and Tin (Sn) in an alloy for each of room temperature, 100 degrees Celsius, 200 degrees Celsius, 300 degrees Celsius, 400 degrees Celsius, 500 degrees Celsius, 600 degree Celsius, and 700 degrees Celsius. For example, if the observed proportion by mass in a particle is 85% copper, 8% zinc, and 7% tin, the processor may estimate that the temperature at the time the particle separated was around 500 degrees Celsius. In some embodiments, observed proportions might not match reference data exactly, and the temperature estimate may be determined through, for example, interpolation between different entries in the reference data. It will be appreciated that FIG. 5 is merely an example mapping of temperature and that in some embodiments, other environmental factors may affect the mapping of composition to temperature. As another example, an observed chemical composition or proportion by mass of tin, copper and lead in the particles 124 may be used in conjunction with a mapping of the composition of leaded bronze with temperature (or other relationship data between chemical composition and exposure temperature, such as FIG. 3) in order to determine an estimate of the temperature at the time the particle 124 was separated from an engine component.

In some embodiments, the estimate of the temperature signifies that the temperature experienced by the outer surface of an engine component may have reached at least that temperature. Therefore, in some embodiments, the estimated temperature may correspond to a maximum temperature reached by the component. In some embodiments, the estimate denotes that the component reached at least the estimated temperature, but it is possible that maximum temperature experienced could have exceeded the estimate. For example, in a condition in which temperature is rising, a particle of debris may enter the lubricating fluid. It is possible that the temperature continues to rise, without another particle of debris entering the lubricating fluid. As such, the debris might be indicative of the temperature at the point in time in which the particle was created (which would be less than the maximum temperature experienced). In some embodiments, it can be inferred that if the outer surface of the engine component reached at least the estimated temperature, then the particular area of the engine in which the component is located may have also reached at least the estimated temperature. For example, if one particular area of the engine contains a component made of leaded bronze and no other area of the engine does, then it can be inferred that the composition of the alloy particles filtered from fluid 126 may correspond to the temperature experienced by the area of the engine in which the particular component is located.

The composition of alloy particles retrieved from fluid 126 may be independent of the current temperature of the oil. For example, the surface composition of an alloy changes with temperature, and it is reasonable to assume that only particles from the outermost surface of the component will form part of the debris which is ultimately found in fluid 126. The composition of the debris found in fluid 126 will not subsequently change composition.

As such, the engine can be turned off, and the ambient temperature may begin to decrease, but this will not affect the composition of the alloy particles which have already worn off the engine component and are now in the fluid 126. Since the composition of alloy particles in fluid 126 will remain unchanged as the temperature of the fluid cools down, the composition may provide a reliable indication that a component made from that alloy experienced at least a certain temperature.

A previous approach to determining the temperature reached by a particular engine component is to remove the component from an engine, visually inspect the component, and look for visual evidence (e.g. a change in color) which may be indicative of that a particular temperature was reached. However, this is labor-intensive and not particularly precise or reliable. Contrastingly, the use of alloy particles filtered from fluid 126 may provide a relatively easy and reliable way of determining that the component or the engine reached at least a particular exposure temperature based on known relationships between alloy composition and temperature.

In some embodiments, reference data 134 may include historical data which represents known correlations between composition of alloy particles and temperatures reached by a particular engine model. Such known correlations may simplify the process of determining the temperature reached by a particular component or a particular engine.

Since an engine may be running for an extended period of time at different temperatures, it is possible that the highest ranges of temperature may only be reached for a relatively small proportion of the time the engine is in operation. As such the debris or particles 124 which are found in fluid 126 may largely correspond to debris which was produced during lower temperatures of operation, with relatively small amounts of debris with a different composition (i.e. obtained at higher temperatures).

Moreover, it is contemplated that the rate at which debris or particles 124 are produced may vary with temperature. For example, it is possible that an engine operating at 120 degrees Celsius in a particular region may not generate any debris, whereas an engine operating at 350 degrees Celsius in that region may generate many debris particles.

In some embodiments, reference data 134 may be normalized to account for expected alloy compositions in particles during expected operating conditions, such that unexpected alloy compositions in particles 124 are more easily identified and mapped to the correct exposure temperature by computer 112. In some embodiments, the composition of each individual alloy particle may be measured, and an estimate of the temperature at the time of that particle's separation from the engine component may be determined. In some embodiments, the temperature reached by the engine component being made of the alloy may be estimated by determining the exposure temperature of a plurality of particles extracted from the oil. In some embodiments, an estimate of a maximum exposure temperature may be determined by selecting the highest temperature estimate from among a plurality of temperature estimates determined by analyzing a plurality of particles 124. In some embodiments, a local minimum exposure temperature may be determined (e.g. by concluding that in order for a particular particle 124 composition to have occurred, the temperature had to have reached at least a particular minimum temperature).

In an example where a fluid sample 126 from an engine is being analyzed, data obtained for the specific fluid sample 126 may be compared with other historical data obtained from engines of the same or similar type obtained at equivalent or similar operating hours and/or equivalent or similar operating conditions (e.g. running in a dry or sandy environment vs. a wet environment).

Historical data may be collected as part of the methods and systems described herein, may be collected using other techniques, may be collected as part of routine maintenance, may be derived from previous records and engine specifications, or may be obtained by any other suitable means. One or more sets of historical data may be represented by an aggregate or general historical model of expected engine wear and/or expected alloy composition for a given engine type. A historical model may be a simple average of all data for a given engine type at a given operating age, for example. In some embodiments, a historical model may include an average of all data, expunged of six-sigma results. The model may be adjusted over time as more historical data sets are added to the model. A model based on a larger population of historical data may be a more accurate and precise predictor temperature than a model based on a smaller population of historical data. Historical data may include data from different engines of the same engine type at the same or similar operating hours (also referred to as latitudinal data or cross-sectional data), and may also include data from the same engine at different operating hours (also referred to as longitudinal data).

The comparison between the sample data and the reference data 134 may be carried out using any statistical methods. For example, if a composition of a particular alloy particle 124 falls outside a three sigma range of the historical data, this may be flagged or highlighted. For example, for a given category the comparison may use the calculation: (sample data—average data)/standard deviation.

At 430, a prediction is made as to the exposure temperature experienced by the engine and/or component. This prediction may be based on the results of the comparison with reference data 134. In some embodiments, the prediction may be based on a comparison of alloy particle compositions and a relationship or lookup table which maps particle compositions to temperature. In some embodiments, the prediction may be based on a comparison of alloy particle compositions with a combination of a relationship between particle compositions to temperature, as well as historical data from the same engine or engine type.

At 435, an output is generated based on the estimated exposure temperature. Such outputs may include, for example, notifications or alerts to the user that maintenance or inspection is required, a notification of the temperature reached, a notification that the temperature is within expected ranges, or the like. In some embodiments, a maintenance action relative to the engine may be performed based on the output. For example, some maintenance actions may include corrective actions, inspecting the engine, inspecting a particular component or area of the engine, adding additional lubrication to the engine, changing the oil, overhauling the engine, or the like. Other example maintenance actions may include, for example, updating a maintenance status of the engine (e.g. tracking a state of wear of the engine or component(s) of the engine, tracking a calculated time before the next inspection of the engine, or the like).

In some embodiments, an estimated exposure temperature which is significantly higher or lower than the expected temperature may indicate that corrective action is necessary. For example, a higher than expected temperature may indicate an underlying problem with the engine. Such problems may include, for example, excess vibration, bearing rubbing, gear degradation, bearing cage and race degradation, lack of lubrication, or the like. Maintenance or corrective actions which may be taken may include, for example, inspecting the engine, inspecting a particular component or area of the engine, and/or adding additional lubrication to the engine, as well as other maintenance actions.

A particular engine type may be known to have certain failure patterns, based on historical data. By comparing data for a given engine belonging to that category/sub-category with historical data for that category/sub-category, it may be possible to predict a particular cause or failure mechanism for the increase in temperature experienced by the engine. For example, historical data may reveal certain patterns of engine temperature or patterns of alloy particle characteristics over time. By comparing the sample particle data of the given engine with the historical pattern over time, a prediction may be generated. Output 435 may include a prediction of failure.

Using the generated prediction of failure, appropriate action may be taken. For example, where failure of a particular component has been predicted, that component may be replaced and/or monitored with greater frequency, or that engine may be placed on a tighter maintenance schedule and/or oil analysis schedule. In some embodiments, the disclosed methods may include performing a maintenance action or pre-maintenance action on the engine. Maintenance or pre-maintenance actions may include, for example, flagging the engine for maintenance (e.g. in a maintenance file), generating a notification to alert a user for the need to perform maintenance, scheduling maintenance for the engine, and performing the appropriate maintenance, among others.

In some embodiments, a generated prediction may be recorded and saved for further action and/or future reference. The results may also be added to the historical data. An electronic image of the fluid sample 126 may also be stored for future reference and/or further processing.

Figure 6:
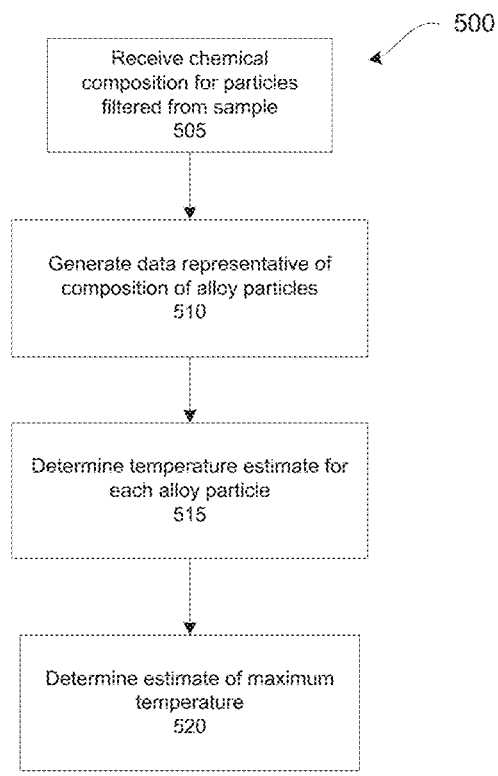
FIG. 6 is a flowchart illustrating an example method for determining an exposure temperature in an engine.

FIG. 6 is a flowchart illustrating a method 500 for improving a condition of an engine such as a gas turbine engine of an aircraft. In some embodiments, method 500 may be used to predict a failure or wearing of one or more components of the engine and suggest corrective action. Method 500 may be performed in its entirety or in part using system 100 shown in FIG. 1 and described above. Method 500 or parts thereof may be performed in combination with parts of other methods disclosed herein. Aspects of the systems and methods described above may also apply to method 500. Some or all of method 500 may be computer-implemented.

Method 500 may include the determination of a chemical composition or mass of one or more particles 124 and/or the mass of one or more elements, alloys or material types contained in one or more particles 124. In the case of alloy particles, the particular composition of the alloy particles 124 filtered from fluid sample 126 may be used to identify the particular engine component from which the particle originated and/or determine the exposure temperature experienced by the particle, or by the area of the engine in which the component corresponding to the particular alloy is located.

For example, method 500 may provide an indication of how much mass of each constituent of a particular alloy is present in sample 126 of lubricating fluid. For example, method 500 may provide an indication of how many micrograms of tin, copper and lead (i.e. the constituents of leaded bronze) are present per litre of lubricating fluid. A mapping of alloy composition to temperature can then be used to determine the exposure temperature experienced by the engine.

Performing method 500 using samples 126 of lubricating fluid obtained from an engine at different times may provide an indication as to whether a particular condition (e.g. wear mechanism, overheating, or the like) is active and whether the condition is progressing. For example, the composition of each constituent of an alloy in a subsequent fluid sample 126 may indicate that the exposure temperature has increased relative to the exposure temperature reached at the time of a previous sampling.

In some embodiments, method 500 may include receiving input data 128 at 505 representative of a respective chemical composition for a plurality of particles 124 filtered from a sample 126 of used lubricating fluid obtained from an engine. In some embodiments, the particles 124 include alloy particles. At 510, data representative of the composition of the alloy particles is generated based on the input data using data acquisition equipment. At 515, a temperature is estimated for each particle. In some embodiments, an exposure temperature is estimated by comparing the measured alloy composition with reference data 134. At 520, an estimate of the maximum temperature of the engine may be generated.

In some embodiments, a temperature estimate may be determined for each alloy particle. Each alloy particle may have worn from a surface of an engine component at different moments in time with different temperatures, which would result in alloy particles having different compositions depending on the temperature at the time of wear. As such, the composition of alloy particles 124 may vary. In some embodiments, the temperature experienced by the engine is determined by selecting the highest exposure temperature estimate from among the alloy particles analyzed.

As noted above, reference data 134 may include mappings of alloy composition profiles to particular temperatures. For example, reference data 134 may include particular points from the relation shown in FIG. 3 for an alloy which includes lead and tin. As such, if one or more particles 124 are found to have a composition which roughly corresponds to a composition in reference data 134, the system 100 may determine that the exposure temperature was a particular temperature during operation of the engine.

In some embodiments, reference data 134 may include predefined engine diagnosis rules obtained from a database stored in memory 118 or elsewhere and used for evaluation of the temperature reached by the engine. Such rules may include ranges and threshold compositions of alloy particles in lubricating fluid for different types of alloys which may be indicative of different conditions (e.g. wear mechanisms, failure signs) of the engine. Accordingly, comparison of the alloy particle compositions with reference data 134 may be useful in diagnosing a condition of the engine. In some embodiments, method 500 may include using output data representative of the exposure temperature reached by the engine to initiate a corrective action such as a maintenance procedure or some recommended inspection task/schedule based on the output data. In some embodiments, such corrective actions may be based on the predefined engine rules.

For example, if a temperature reached by the engine exceeds a threshold value, the predefined rules may cause an alert or notification to a user that the engine is in need of urgent inspection. Such inspection might reveal, for example, an abnormal wearing of bushings during operation.

The present disclosure also provides systems for carrying out the disclosed methods. The disclosed methods and systems may allow for monitoring of an engine over time, and may allow for a timeline of expected failure mechanisms to be developed for that engine type based on the exposure temperature experienced by engine components during points of operation.

Of course, the above described embodiments are intended to be illustrative only and in no way limiting. The described embodiments are susceptible to many modifications of form, arrangement of parts, details and order of operation. The invention is intended to encompass all such modification within its scope, as defined by the claims.

What is claimed is:

1. A method for determining an exposure temperature in an engine, the method comprising:
   receiving input data representative of a chemical composition of a particle filtered from a lubrication fluid of the engine;
   using one or more data processors:
      comparing the chemical composition of the particle with reference data including a relationship between the chemical composition and the exposure temperature of the particle;
      based on the comparing, determining the exposure temperature of the particle; and
      generating an output based on the exposure temperature of the particle; and
   performing a maintenance action relative to the engine based on the output.

2. The method of claim 1, wherein the relationship between the chemical composition and the exposure temperature of the particle is a function of alloy constituents in the particle.

3. The method of claim 1, wherein the composition of the particle is by proportion by mass of constituents of the particle.

4. The method of claim 1, wherein the particle includes tin, copper and lead and the relationship between the chemical composition and the exposure temperature is a function of an amount of lead in the chemical composition of the particle.

5. The method of claim 1, further comprising:
   obtaining a fluid sample from the engine; and
   filtering the fluid sample to obtain the particle from the fluid sample.

6. The method of claim 1, wherein the output comprises an indication of the maintenance action.

7. The method of claim 1, wherein the one or more data processors are configured to identify a component of the engine associated with the particle based on the chemical composition of the particle.

8. The method of claim 1, wherein the exposure temperature represents an estimate of a minimum temperature experienced by a component of the engine.

9. A non-transitory computer-readable storage medium having stored thereon computer-executable instructions that, when executed by a one or more processors, cause the one or more processors to perform the method of claim 1.

10. The method of claim 1, wherein receiving the input data comprises obtaining the input data representative of the chemical composition for the particle using data acquisition equipment.

11. The method of claim 10, wherein the data acquisition equipment is an X-ray fluorescence detector.

12. A system for determining an exposure temperature of a component of an engine, the system comprising:
   one or more processors;
   one or more computer-readable storage media having stored thereon processor-executable instructions that, when executed by the one or more processors, cause the one or more processors to perform operations comprising:
      receiving input data representative of a chemical composition of a particle filtered from a lubrication fluid of the engine;
      using the chemical composition of the particle, identifying the component of the engine associated with the particle;
      comparing the composition of the particle with reference data including a relationship between the chemical composition and the exposure temperature of the particle;
      based on the comparing, determining the exposure temperature of the component; and
      generating an output based on the exposure temperature of the component.

13. The system of claim 12, wherein the relationship between the chemical composition and the exposure temperature of the component is a function of alloy constituents in the particle.

14. The system of claim 12, wherein the exposure temperature is a maximum temperature experienced by the component.

15. The system of claim 12, wherein the particle includes tin, copper and lead and the relationship between the chemical composition and the exposure temperature is a function of an amount of lead in the chemical composition of the particle.

16. The system of claim 12, wherein the output comprises an indication of a maintenance action for the engine.

17. A method for improving a condition of an engine, the method comprising:
   receiving input data representative of a composition of a particle filtered from a lubrication fluid of the engine;
   determining an exposure temperature of a component of the engine based on the composition of the particle;
   generating an output representative of a diagnosis of the condition of the engine based on the exposure temperature of the component; and
   performing a maintenance action on the engine to improve the condition of the engine.

18. The method of claim 17, wherein determining the exposure temperature of the component is based on a relationship between the composition of the particle and the exposure temperature of the component as a function of alloy constituents in the particle.

19. The method of claim 17, wherein the component of the engine experienced temperatures of at least the exposure temperature.

20. The method of claim 17, further comprising identifying the component of the engine associated with the particle based on the composition of the particle.

* * * * *